United States Patent [19]

Nemphos et al.

[11] Patent Number: 5,684,213

[45] Date of Patent: Nov. 4, 1997

[54] METHOD FOR THE PREPARATION OF DIALKYL ETHERS

[75] Inventors: Speros Peter Nemphos, League City; Dennis Hearn, Houston, both of Tex.

[73] Assignee: Chemical Research & Licensing Company, Pasadena, Tex.

[21] Appl. No.: 621,221

[22] Filed: Mar. 25, 1996

[51] Int. Cl.$^6$ ................................................ C07C 41/09
[52] U.S. Cl. ........................................ 568/698; 568/699
[58] Field of Search ................................. 568/698, 699

[56] References Cited

U.S. PATENT DOCUMENTS

| | | | |
|---|---|---|---|
| 3,267,156 | 8/1966 | Hansen | 260/614 |
| 3,894,107 | 7/1975 | Butter et al. | 260/668 R |
| 3,931,349 | 1/1976 | Kuo | 260/668 R |
| 4,052,479 | 10/1977 | Chang et al. | 260/682 |
| 4,058,576 | 11/1977 | Chang et al. | 260/673 |
| 4,215,011 | 7/1980 | Smith, Jr. | 252/246 |
| 4,232,177 | 11/1980 | Smith, Jr. | 585/324 |
| 4,443,559 | 4/1984 | Smith, Jr. | 502/527 |
| 4,536,485 | 8/1985 | Topp-Jorgensen | 502/62 |
| 4,542,252 | 9/1985 | Graziani et al. | 585/640 |
| 4,550,217 | 10/1985 | Graziani et al. | 585/324 |
| 4,590,320 | 5/1986 | Sapre | 585/324 |
| 4,857,664 | 8/1989 | Hereng | 568/695 |
| 4,886,918 | 12/1989 | Sorensen et al. | 568/697 |
| 4,906,787 | 3/1990 | Huang et al. | 568/697 |
| 4,935,552 | 6/1990 | Child et al. | 568/695 |
| 5,037,511 | 8/1991 | Dornhagen et al. | 203/37 |
| 5,047,141 | 9/1991 | Chu | 208/120 |
| 5,057,468 | 10/1991 | Adams | 502/1 |
| 5,262,012 | 11/1993 | Smith, Jr. | 220/158 |
| 5,266,546 | 11/1993 | Hearen | 502/300 |
| 5,348,710 | 9/1994 | Johnson et al. | 422/24 |

OTHER PUBLICATIONS

Chang, Clarence D, *Hydrocarbon from Method*, Marcel Decker, 1983.

Chang, Clarence D, "Process Studies on the Conversion of Methanol to Gasoline", *Ind. Eng. Chem. Process. Der. Des.*, vol. 17, No. 3, 1978, pp. 255–260.

*Primary Examiner*—Marianne M. Cintins
*Assistant Examiner*—Dwayne C. Jones
*Attorney, Agent, or Firm*—Kenneth H. Johnson

[57] ABSTRACT

A method for producing dialkyl ethers comprising feeding a stream containing a $C_1$ to $C_4$ alcohol to a distillation column reactor into a feed zone, contacting the stream with a fixed bed zeolite prepared as a distillation structure to form the corresponding dialkyl ether and water, and concurrently fractionating the ether product from the water and unreacted materials wherein the improvement is the addition of a small amount of hydrogen to the reaction zone to inhibit catalyst fouling and substantially increasing the catalyst life and activity.

22 Claims, 2 Drawing Sheets

METHOD FOR THE PREPARATION OF DIALKYL ETHERS

BACKGROUND OF THE INVENTION

1. Field of the Invention

The present invention relates to an improvement in the preparation of dialkyl ethers by catalytic reaction of the corresponding alcohol with itself and the concurrent distillation and separation of the product, by-products and reactants. More particularity the invention relates to procedure that substantially extends the catalyst life.

2. Related Art

The preparation of ethers by the dehydration of alcohols using an acid is known, e.g.,

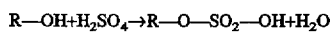

Hansen in U.S. Pat. No. 3,267,156 discloses that acidic cation exchange resins effectively catalyze the selective dehydration of alcohols to ethers as exemplified by the production of diisopropyl ether.

A method of carrying out catalytic reactions has been developed wherein the components of the reaction system are concurrently separable by distillation using the catalyst structures as the distillation structures. Such systems are described variously in U.S. Pat. Nos. 4,215,011; 4,232,177; 4,242,530; 4,250,052; 4,302,356; 4,336,407; 4,439,350 and 4,307,254 commonly assigned herewith. In addition, commonly assigned U.S. Pat. No. 4,443,559, 5,057,468, 5262, 012 5,266,546 and 5,348,710 disclose a variety of catalyst structures for this use and are incorporated by reference herein.

SUMMARY OF THE INVENTION

The present invention is a process for producing dialkyl ethers by the catalytic dehydration of the corresponding alcohol in the presence of hydrogen in a distillation column reactor. More particularly the invention relates to the preparation of dimethyl ether, diethyl ether, dipropyl ether and dibutyl ether from the dehydration of the corresponding $C_1$ to $C_4$ alcohols in the presence of hydrogen. The hydrogen may conveniently be injected into column as a small bleed stream. Significant improvement in the catalyst life before regeneration results from the hydrogen being present in the column during the reaction and distillation. It is believed that the hydrogen inhibits polymerization and carbonization on the catalyst, thus increasing the catalyst life. The hydrogen should be injected continuously. Based on the alcohol feed the amount of hydrogen is about 0.0001 to 0.0010 and more preferably 0.0002 to 0.0007 mole per mole of alcohol.

DETAILED DESCRIPTION OF THE PREFERRED EMBODIMENTS

Figure 1:
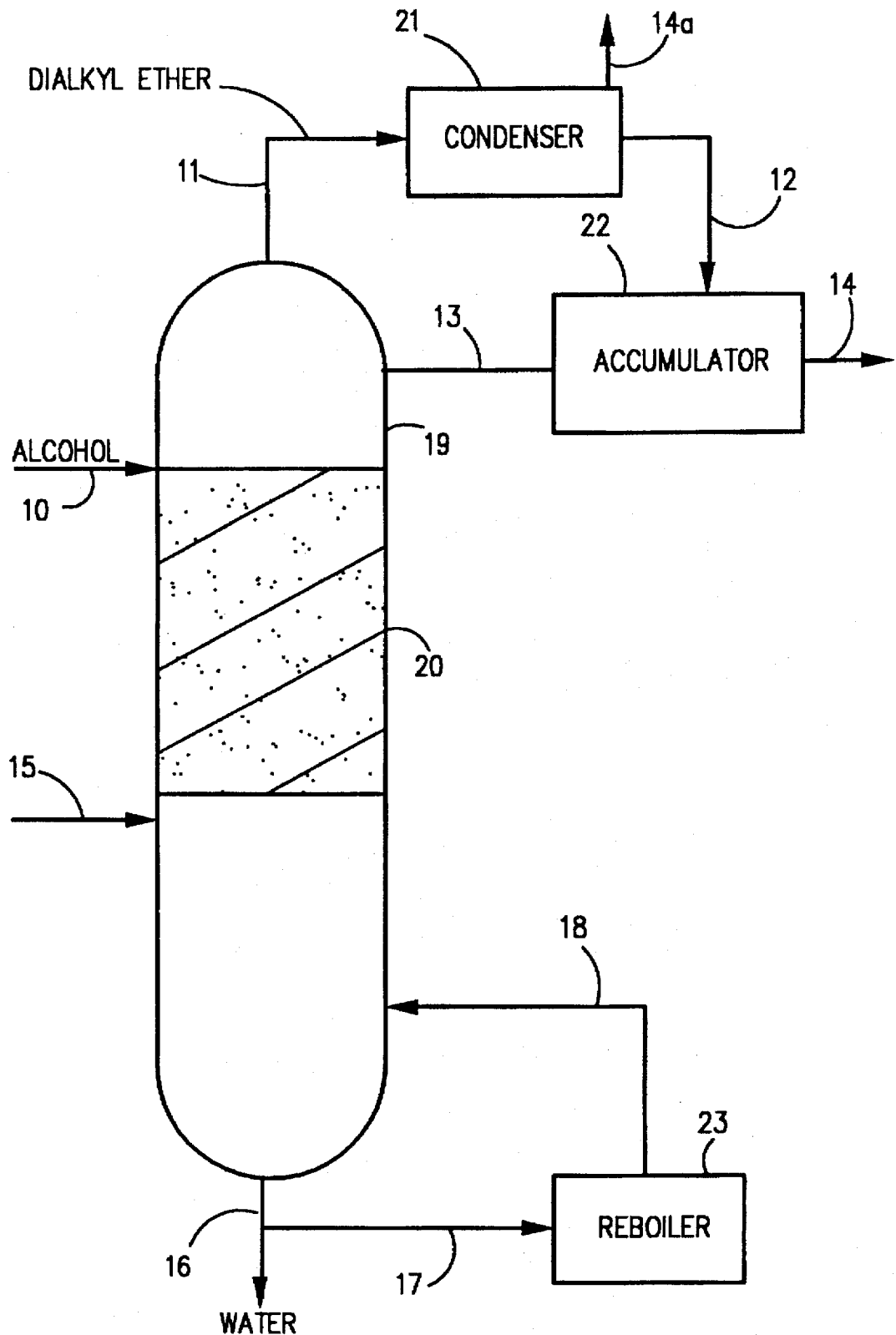
FIG. 1 shows a schematic representation of the process of the present invention for producing dimethyl-, diethyl- and dipropyl ethers.

One embodiment is an improvement in the process for producing dimethyl-, diethyl- and dipropyl ethers comprising the steps of:

(a) feeding a stream containing an alcohol selected from the group consisting of methanol, ethanol and propanol to a distillation column reactor into a feed zone, (b) concurrently:
 (1) contacting said stream with a fixed bed zeolite, catalytic distillation structure in a distillation reaction zone thereby catalytically reacting at least a portion of said alcohol to form the corresponding dialkyl ether and water, and
 (2) fractionating the resultant dialkyl ether product from water and unreacted material, and (c) withdrawing the dialkyl ether from the distillation column reactor at a point above said distillation reaction zone and (d) withdrawing water at a point below said distillation reaction zone; wherein the improvement comprises carrying out said reacting and fractionating in the presence of added hydrogen.

Another embodiment is an improvement in the process for producing di-normal butyl ether by a process comprising the steps of:

(a) feeding a stream containing n-butanol to a distillation column reactor in a feed zone, (b) concurrently:
 (1) contacting said stream containing n-butanol with a fixed bed cation exchange resin packing in a distillation reaction zone thereby catalytically reacting a portion of the n-butanol to form di-n-butyl ether, and
 (2) fractionating the resultant di-n-butyl ether product from water and unreacted material, and (c) withdrawing the di-n-butyl ether from the distillation column reactor at a point below said distillation reaction zone and (d) withdrawing unreacted n-butanol and water at a point above said distillation reaction zone;

wherein the improvement comprises carrying out said reacting and fractionating in the presence of added hydrogen.

In both cases the alcohol stream in the distillation reaction zone as well as the products are in both vapor and liquid phase, just as the materials in a standard packed distillation column. As a result the reaction may proceed in both phases with the apparent reaction rate being higher than expected. Because the reaction is occurring concurrently with distillation, the initial reaction product is removed from the reaction zone as quickly as it is formed and thus cannot contribute to the reverse reaction (Le Chatelier's Principle).

The temperature in the column is determined by the boiling point of the liquid mixture present at any given pressure. The temperature in the lower portions of the column will reflect the constitution of the material in that portion of the column, and will be higher than the overhead; that is, at constant pressure a change in the temperature indicates a change in the composition in the column. To change the temperature the pressure is changed. Temperature control in the reaction zone is thus controlled by the pressure with the addition of heat (the reactions being endothermic) only causing more boil up. By increasing the pressure the temperature is increased, and vice versa.

CATALYST AND DISTILLATION STRUCTURE

Naturally occurring zeolites have irregular pore size and are not generally considered as equivalent to synthetic zeolites. In the present invention, however, naturally occurring zeolites are acceptable so long as they are substantially pure. The balance of the present discussion shall be directed to the synthetic zeolites with the understanding that natural zeolites are considered equivalent thereto as indicated above, i.e. in so far as the natural zeolites are the functional equivalents to the synthetic zeolites.

Usually synthetic zeolites are prepared in the sodium form, that is, with a sodium cation in close proximity to each aluminum tetrahedron and balancing its charge. A number of principal types of molecular sieves have been reported, A, X, Y and L erionite, omega, beta and mordenite. The A type have relative small pore size. By the term pore size is meant the effective pore size (diameter) rather than the free pore size (diameter). Types X and Y have larger pore size (approximately 7.4 Å.) and differ as to the range of ratio of $Al_2O_3$ to $SiO_2$ as:

Type X————$Al_2O_3$/2.0–3.0 $SiO_2$

Type Y————$Al_2O_3$/3.0–6.0 $SiO_2$

Type L and other types listed have still higher ratios of $SiO_2$ to $Al_2O_3$

The zeolite catalysts employed in the present invention are the acid form or exhibit acidic characteristics. The acid form is commercially available, but also may be prepared by treating the zeolites with acid to exchange Na for hydrogen. Another method to produce the acid form is to treat the zeolite with decomposable cations (generally ammonium ions) to replace Na with the decomposable ions and thereafter to heat the mole sieve to decompose the cation leaving the acid form. Generally the Na form is treated with ammonium hydroxide to remove the Na and thereafter the zeolite is heated to a temperature of about 350° C. to remove the ammonia. The removal of $Na^+$ ions with $NH^+_4$ is more easily carried out than with multivalent ions as described below and these catalysts are generally more active, but less stable to heat than the multivalent cation exchange forms. Zeolites, which have had their alkali metal reduced to low levels by partial treatment with $NH^+_4$ and partial multivalent metal cation exchange, may be expected to possess increased activity and increased stability.

It would appear that the pore size within the crystal lattice is significant in this reaction. According to one theory of molecular sieve catalytic activity, zeolite catalysis occurs primarily inside the uniform crystal cavities, consequently zeolitic catalyst activity depends on the number of aluminum atoms in the crystal and thus on the chemical composition of the crystal. Moreover, these catalytic sites are fixed within the rigid structure of the crystal, so that access to site can be altered by altering the structure of the crystal.

The particulate zeolites may be employed by enclosing them in a porous container such as cloth, screen wire or polymeric mesh. The material used to make the container must be inert to the reactants and conditions in the reaction system. Particles of about 0.15 mm size or powders up to about ¼ inch diameter may be employed in the containers.

The container employed to hold the catalyst particles may have any configuration, such as the pockets disclosed in the commonly assigned patents above or the container may be a single cylinder, sphere, doughnut, cube, tube or the like.

It is not essential that the spacing component, entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

In the following examples the catalyst packing consisted of a flexible, semi-rigid open mesh tubular element filled with a particulate catalytic material (catalyst component) and sealed at both ends, intimately associated with and supported by a wire mesh screen. The flexible, semi-rigid open mesh tubular element filled with a particulate catalytic material preferably has a fastener every 1–12 inches along the length of the tube to form a multiple link shaped catalytic distillation structure. The links formed by the fasteners may be evenly or irregularly spaced.

The wire mesh provides the support for the catalyst/wire mesh tube and provides some degree of vapor passage through the catalyst particles, which otherwise form a very compact bed which has a high pressure drop. Thus, the down flowing liquid is in intimate contact with the rising vapors in the column.

PROCESS DESCRIPTION

The manner of operating the distillation column reactor, i.e., the severity of the conditions, is determined by the operator to achieve the desired result. The pressure of the column is increased until the desired extent of reaction is obtained. For the $C_1$ to $C_3$ alcohol conversion this pressure should be in the range of 20–1000 psig where the temperature will be from 130° to 300° C. with the preferred pressure range being between 180 to 600 psig at temperatures of 130° to 250° C. For the n-$C_4$ alcohol feed the pressure range is between 0 to 200 psig yielding temperatures in the range of between 118° to 250° C. with the preferred pressure range being between 85 to 135 psig at temperature of between 175° and 232° C. The alcohol preferably comprises 40 to 100% of the feed stream.

The reaction system can be described as heterogeneous since the catalyst remains as a distinct entity. The catalyst may be employed in such conventional distillation packing shapes, as Rashig rings, Pall rings, saddles or the like. Similarly, the catalyst may be employed in granular or extrudate form as described herein above.

Bulk type liquid phase reactions have as one problem the control of the temperature. The distillation avoids the problem entirely. The success of the catalytic distillation approach lies in an understanding of the principles associated with distillation. First, because the reaction is occurring concurrently with distillation, the initial reaction product, the dialkyl ether, is removed from the reaction zone nearly as quickly as it is formed. This removal of the ether minimizes decomposition of the ether which is catalyzed by the same catalyst. Second, the temperature of the reaction is controlled by the boiling point of the mixture in the reactor at the system pressure. The heat of the reaction, which is endothermic, simply consumes more boil up, but no change in temperature. That is, if the heat is added in excess, there is no harm done since the excess will only result in more boil up. Third, the reaction has an increased driving force because the reaction products have been removed and cannot contribute to the reverse reaction (Le Chatelier's Principle).

As a result, a great deal of control over the rate of reaction and distribution of products can be achieved by regulating the system pressure. Also, adjusting the throughput (liquid hourly space velocity$^{-1}$=residence time) gives further control of product distribution.

A reflux is preferably included in the system. The reflux ratio could vary over the rate of 0.5 to 25:1. In runs of relative short duration no problem with catalyst fouling was observed, however where longer runs were undertaken for commercial process viability, the catalyst became fouled, by polymers and/or carbon to reduce the activity of the catalysts at around 200–300 hours, with total deactivation occurring at 600–1000 hours.

Hydrogen is added below the catalyst bed. Since only a small amount of hydrogen is necessary to inhibit the fouling of the catalyst a small bleed of hydrogen generally only a few parts per million may suffice. The hydrogen should be supplied continuously. A continuous feed of hydrogen is a simple means to keep the catalyst free of fouling agents. The small amounts of hydrogen used were not observed to adversely affect the dehydration or cause any loss of product.

A. Production of Dimethyl-, Diethyl- and Dipropyl Ethers

In this reaction both the ether product and water must be removed to force the reaction to completion. The water is removed as bottoms, with possible alcohol contamination, and the dialkyl ether as overhead. The recovery of the product in this embodiment is relatively simple since water does not form an azeotrope with either dimethyl-, diethyl- or dipropyl ether.

Mordenite is a preferred catalyst for the reaction, particularly for the dimethyl ether, because this zeolite has a relatively small pore size. Generally pore size of 3 to 5 Å are preferred for this group of reactants. In the case of methanol, catalyst fouling may also be reduced by removing formaldehyde impurities from the methanol feed.

B. Production of Di-n-butyl Ether

As in the conversion of the $C_1$ to $C_3$ alcohols both the ether product and water must be removed to force the reaction to completion. The water is removed as an azeotrope with butanol and the butyl ether in the overhead. Quite fortuitously, when the overhead is condensed and accumulated, two phases result, i.e., a lower phase which is about 95% water and an upper phase which contains only about 5% water. The upper phase is preferably recycled to the reactor as reflux and the lower water phase removed for purification and disposal. The preferred zeolites for this reaction generally have larger pore size than for the smaller molecules for the $C_1$ to $C^3$ alcohols. Suitable pore size is in the range of 5 to 8 Å.

EXAMPLE 1

Production of Dimethyl Ether

Operation of the particular embodiment for converting the $C_1$ to $C_3$ alcohols to the corresponding dialkyl ethers can be readily understood from a consideration of FIG. 1. The reactor is a 25 foot, 1 inch diameter tower having the following configuration:

middle 10 feet, 190 grams mordenite 1/16" packed in 6"×0.75" tubular (sausages) wrapped in stainless steel 100 mesh screen remaining 15 feet packed with ceramic saddles (7.5' top and bottom).

Referring to FIG. 1, the embodiment is illustrated by the production of dimethyl ether (DME). Methanol 10 is fed at the upper end of (or somewhat above) the catalyst bed 20 in reactor 19. The exact location of the feed is not critical, however, location of feed at different points will, of necessity, result in changes in the conditions to obtain the requisite contact of the feed with the catalyst and the concurrent fractionation. The location of feed to optimize the function of the process is easily carried out by those operating in the field. Moreover, the characteristics of each individual process needs to be ascertained for optimum operation. Hydrogen can be added through line 15, which is below the catalyst bed. After an initial run without hydrogen, the catalyst was replaced with fresh catalyst and hydrogen was added as a bleed into the reactor and another run carried out.

The overhead 11 comprises dimethyl ether which is condensed in condenser 21 and fed via 12 to accumulator 22; a portion of which is returned as reflux via 13 and a portion recovered via 14. Hydrogen also exits in the overhead and is not condensed, being removed by 14a.

The bottoms portion are recovered via 16 and are primarily water. A reboiler 23 is provided to recycle a portion of the bottoms via 17 and 18. To illustrate this embodiment a typical operation using 99+% methanol feed is provided. The conditions and character of each stream are provided below in tabular form in TABLE I.

The overhead stream 14 may be fractionated to 99.9+% DME product recovered.

TABLE I

| PRODUCTION OF DIMETHYL ETHER | | | | | |
|---|---|---|---|---|---|
| Stream | 10 | 15 | 11 & 12 | 14 | 16 |
| (Run 30-11) 450 hours on stream Pressure 600 psi Temperature, °C. Catalyst Zone 350–400 Component (lb/hr) | | | | | |
| Methanol | 3 | | | 1.7 | 0.92 |
| Dimethyl Ether | | | | 0.3 | |
| Water | | | | | 0.08 |
| Hydrogen | | 0 | | | |
| (Run 30-12) 450 Hours on stream Pressure 600 psi Temperature, °C. Catalyst Zone 350–400 Component (lb hr) | | | | | |
| Methanol | 3 | | | 0.9 | 0.5 |
| Dimethyl Ether | | | | 1.1 | |
| Water | | | | | 0.5 |
| Hydrogen (SCF/hr) | | 0.1 | | | |

EXAMPLE 2

Production of Di-n-Butyl Ether

Figure 2:
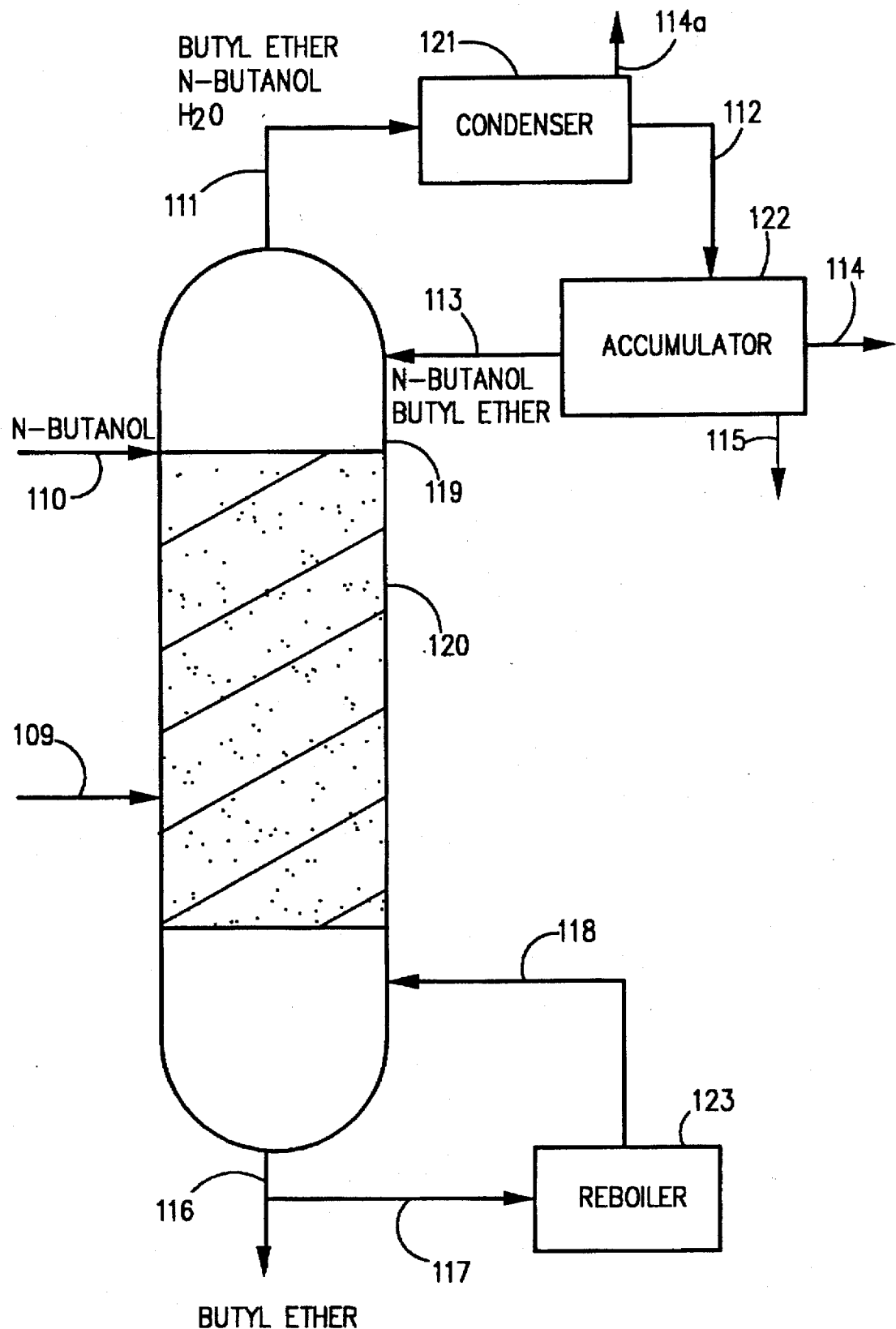
FIG. 2 shows a schematic representation of the process of the present invention for producing di-n-butyl ether.

Operation of the embodiment for the production of di-n-butyl ether can be readily understood from a consideration of FIG. 2. The catalyst used was Y-84 zeolite produced by UOP. The reactor is a 25 foot, 1 inch diameter tower having the following configuration:

middle 10 feet, 190 grams EBZ-150 1/16" packed in 6"×0.75" tubular (sausages) wrapped in stainless steel 100 mesh screen remaining 15 feet packed with ceramic saddles (7.5' top and bottom).

Referring again to FIG. 2 n-butanol 110 is fed at approximately 1/4 of the length down the catalyst bed 120 in reactor 119. The exact location of the feed is not critical, however, it is preferred that the feed be made into the catalyst packing to initiate the reaction. Hydrogen can be added to the column via 109 below the catalyst bed. The overhead 111 comprises an azeotrope of n-butanol, butyl ether, and water and hydrogen when added. This mixture, except for hydrogen, is condensed in condenser 121 and fed via 112 to accumulator 122 where the phases separate. Hydrogen is removed via 114a. The upper layer is principally n-butanol and butyl ether, a portion of which is returned as reflux via 113 and a portion recovered for recycle or other use. The water phase (bottom phase) is removed via line 115 and can be fractionated to recover the alcohol. The bed temperature is in the range of 180°–216 °C.

The bottoms portion is recovered via 116 and is high purity di-n-butyl ether. A reboiler is provided to recycle a portion of the bottoms via 117 and 118. To illustrate this embodiment a typical operation using 100% n-butanol feed is provided. The conditions and character of each stream are provided below in TABLE II. The initial pressure was 100 psi and was increased to 150 psi at 500 hours on stream. Hydrogen was added continuously.

TABLE II

PRODUCTION OF DI-N-BUTYL ETHER

Pressure 150 psig

| Stream | 109 | 114 | 115 | 116 |
|---|---|---|---|---|
| Component (lbs/hr) | | | | |
| n-butanol | 3 | 1.3 | 0.02 | 0.15 |
| Butyl ether | | | | 1.35 |
| Water | | | 0.18 | |
| Hydrogen (SCF/hr) (10% in Nitrogen) | 3 | | | |

The invention claimed is:

1. In a process for the production of dialkyl ether comprising the steps of:
   (a) feeding a stream containing an alkyl alcohol to a distillation column reactor into a feed zone,
   (b) concurrently:
      (1) contacting said stream containing said alcohol with a fixed bed zeolite catalyst prepared as a distillation structure in a distillation reaction zone thereby catalytically reacting at least a portion of said alcohol to form the corresponding dialkyl ether and water, and
      (2) fractionating the resultant dialkyl ether product from water and unreacted material,
   (c) withdrawing the dialkyl ether product from the distillation column reactor as a first stream containing substantially pure dialkyl ether, and
   (d) withdrawing water and unreacted material from the distillation column as a second stream; wherein the improvement comprises carrying out said reacting and fractionating in the presence of added hydrogen.

2. The process according to claim 1 wherein said alcohol is selected from the group consisting of methanol, ethanol, propanol or normal butanol.

3. The process according to claim 2 wherein said alcohol is selected from the group consisting of methanol, ethanol or propanol, and: (1) said first stream is withdrawn from said distillation column reactor at a point above said distillation reaction; (2) said water is separated from said unreacted material in a distillation zone below said distillation reaction zone and withdrawn as bottoms.

4. The process according to claim 3 wherein said zeolite catalyst consists of mordenite.

5. The process according to claim 4 wherein the pressure in the column is in the range of 20 to 1,000 psig.

6. The process according to claim 5 wherein the temperature is the range of 130° to 300° C.

7. The process according to claim 5 wherein the temperature in said distillation reaction zone is the boiling point of the reaction mixture under the pressure conditions therein.

8. The process according to claim 3 wherein said alcohol is methanol and said dialkyl ether is dimethyl ether.

9. The process according to claim 6 wherein the pressure in the column is in the range of 180 to 600 psig, and the temperature is in the range of 130° to 250° C.

10. The process according to claim 1 wherein said alcohol comprises 40 to 100% of the feed stream.

11. The process according to claim 3 wherein said alcohol is ethanol and said dialkyl ether is diethyl ether.

12. The process according to claim 3 wherein said alcohol is propanol and said dialkyl ether is dipropyl ether.

13. The process according to claim 3 wherein a portion of said first stream is returned to said distillation column reactor as reflux.

14. The process according to claim 2 wherein said alcohol is normal butanol and said dialkyl ether is di-n-butyl ether, and: (1) said first stream containing said di-n-butyl ether is withdrawn from said distillation column reactor at a point below said distillation reaction zone; and (2) unreacted normal butanol and water are withdrawn in step (d) as an overhead comprising an azeotrope of normal butanol, di-n-butyl ether and water.

15. The process according to claim 14 wherein the pressure in the column is in the range of 0 to 200 psig.

16. The process according to claim 15 wherein the temperature is in the range of 175° to 232° C.

17. The process according to claim 15 wherein the temperature in said distillation reaction zone is the boiling point of the reaction mixture at the pressure conditions therein.

18. The process according to claim 14 wherein said overhead is condensed and accumulated as a two phase mixture having a top phase comprising mostly normal butanol and a bottom phase comprising mostly water.

19. The process according to claim 18 wherein said phases are separated, and: (1) said bottom phase withdrawn and any alcohol contained therein recovered; and (2) said top phase is withdrawn and a portion thereof returned to said distillation column reactor as reflux.

20. The process according to claim 14 wherein said zeolite comprises Y type zeolite.

21. The process according to claim 1 wherein from 0.0001 to 0.0010 mole of hydrogen is present per mole of alcohol.

22. The process according to claim 1 wherein from 0.0002 to 0.0007 mole of hydrogen is present per mole of alcohol.

* * * * *